United States Patent
Chen et al.

(10) Patent No.: US 11,406,635 B2
(45) Date of Patent: Aug. 9, 2022

(54) SOLID DOSAGE FORMS OF (S)-ETHYL 2-AMINO-3-(4-(2-AMINO-6-((R)-1-(4-CHLORO-2-(3-METHYL-1H-PYRAZOL-1-YL)PHENYL)-2,2,2-TRIFLUOROETHOXY) PYRIMIDIN-4-YL)PHENYL)PROPANOATE

(71) Applicant: TERSERA THERAPEUTICS LLC, Deerfield, IL (US)

(72) Inventors: Jinling Chen, Houston, TX (US); Matthew S. Deaver, Lawrence, KS (US); Richard J. Holl, Lone Jack, MO (US); Kalyan Nuguru, Overland Park, KS (US)

(73) Assignee: TerSera Therapeutics LLC, Deerfield, IL (US)

( * ) Notice: Subject to any disclaimer, the term of this patent is extended or adjusted under 35 U.S.C. 154(b) by 0 days.

(21) Appl. No.: 16/688,658

(22) Filed: Nov. 19, 2019

(65) Prior Publication Data

US 2021/0008068 A1   Jan. 14, 2021

Related U.S. Application Data

(63) Continuation of application No. 15/613,458, filed on Jun. 5, 2017, now abandoned, which is a continuation of application No. 14/619,150, filed on Feb. 11, 2015, now abandoned, which is a continuation of application No. 13/652,527, filed on Oct. 16, 2012, now abandoned.

(60) Provisional application No. 61/547,894, filed on Oct. 17, 2011.

(51) Int. Cl.
*A61K 31/506* (2006.01)
*A61K 9/16* (2006.01)
*A61K 9/20* (2006.01)
*A61K 9/28* (2006.01)

(52) U.S. Cl.
CPC .......... *A61K 31/506* (2013.01); *A61K 9/1623* (2013.01); *A61K 9/1652* (2013.01); *A61K 9/2018* (2013.01); *A61K 9/2054* (2013.01); *A61K 9/2095* (2013.01); *A61K 9/2806* (2013.01); *A61K 9/2893* (2013.01)

(58) Field of Classification Search
CPC combination set(s) only.
See application file for complete search history.

(56) References Cited

U.S. PATENT DOCUMENTS 7,553,840 B2 * 6/2009 Devasagayaraj .... C07D 239/34
514/269

FOREIGN PATENT DOCUMENTS

EP    0 685 231    *   1/1992

OTHER PUBLICATIONS

Chen (A new model for predicting moisture uptake by packaged solid pharmaceuticals, International Journal of Phamaceutics 255, 2003, pp. 217-225).*
Dave (Overview of pharmaceutical excipients used in tablets and capsules, Drug Topics, voice of the Pharmacist, Oct. 24, 2008).*

* cited by examiner

*Primary Examiner* — Kathrien A Cruz
(74) *Attorney, Agent, or Firm* — Levenfeld Pearlstein, LLC

(57) ABSTRACT

Solid pharmaceutical dosage forms comprising (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate (telotristat) are disclosed, as well as methods of making them and compositions useful in their manufacture.

1 Claim, 3 Drawing Sheets

Figure 1:
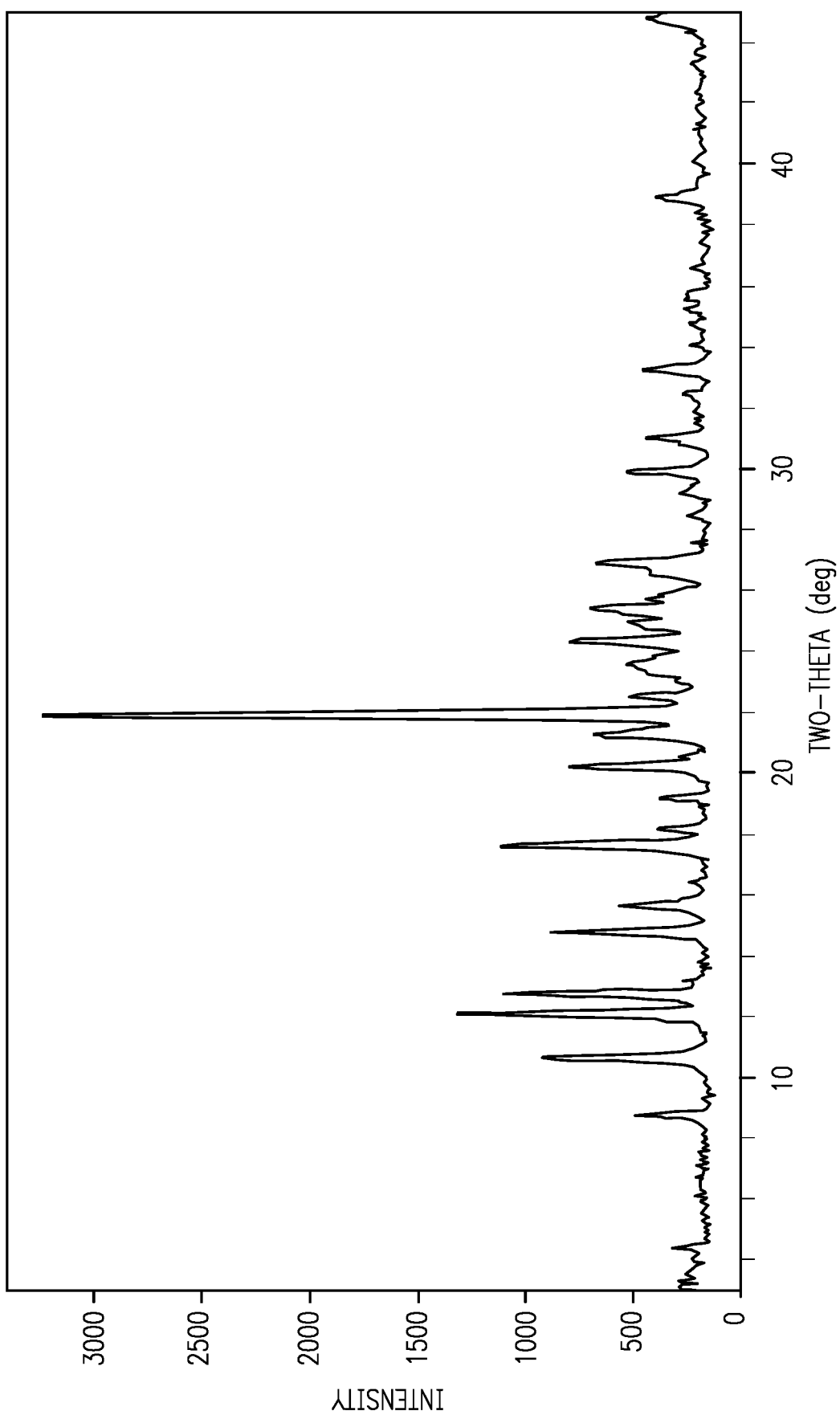

SOLID DOSAGE FORMS OF (S)-ETHYL 2-AMINO-3-(4-(2-AMINO-6-((R)-1-(4-CHLORO-2-(3-METHYL-1H-PYRAZOL-1-YL)PHENYL)-2,2,2-TRIFLUOROETHOXY)PYRIMIDIN-4-YL)PHENYL)PROPANOATE

1. FIELD OF THE INVENTION

This invention relates to solid pharmaceutical dosage forms of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate (telotristat).

2. BACKGROUND OF THE INVENTION

The compound (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate (telotristat) is an inhibitor of tryptophan hydroxylase, the enzyme responsible for the rate-limiting step in biosynthesis of 5-hydroxytryptamine (serotonin). See, e.g., U.S. Pat. No. 7,709,493. The compound is believed to be useful in the treatment of diseases and disorders associated with abnormal levels of serotonin, such as diarrhea-predominant irritable bowel syndrome and carcinoid syndrome. Unfortunately, telotristat's physicochemical properties make its incorporation into a commercially viable dosage form difficult.

Telotristat hydrolyzes when contacted with water. Dosage forms comprising it must, therefore, limit this degradation as much as possible, and must be made using methods that limit the compound's exposure to moisture. The poor flowability of telotristat's crystalline hippurate salt (telotristat etiprate) further complicates the manufacture of dosage forms comprising it. Further adding to the problem is the desire to provide single unit dosage forms that contain at least 100 mg of the compound, and that rapidly release it upon oral administration.

In view of these factors, a need exists for solid dosage forms of telotristat that can be stored at typical temperatures and humidity levels for a commercially viable period of time, and for methods of their manufacture. Preferred dosage forms should be capable of rapidly delivering the compound upon oral administration. A particular need exists for a rapid release tablet formulation of telotristat with good chemical stability, satisfactory oral bioavailability, good processability, and high drug loading.

3. SUMMARY OF THE INVENTION

This invention is directed to solid dosage forms of telotristat. Particular dosage forms are tablets made with the hippurate salt of telotristat (telotristat etiprate).

One embodiment of the invention encompasses a tablet suitable for administration to a patient comprising at least 100, 200, or 300 mg of an active pharmaceutical ingredient (API), which tablet has a disintegration time of less than 10, 5.0, 2.3, 2.0, or 1.8 minutes in water, wherein the API is telotristat or a pharmaceutically acceptable salt thereof.

Another embodiment encompasses a tablet suitable for administration to a patient comprising at least 100, 200, or 300 mg of an API based on free base, which tablet comprises a coating and has a disintegration time of less than 5.5, 4.5, or 4.0 minutes in water, wherein the API is telotristat or a pharmaceutically acceptable salt thereof.

Another embodiment encompasses a tablet having a core consisting essentially of telotristat hippurate, lactose, hyrdroxy propyl cellulose, croscarmellose sodium, magnesium stearate, and silicon dioxide.

Another embodiment encompasses a tablet comprising telotristat or a pharmaceutically acceptable salt thereof, which forms less than 1.0, 0.8 or 0.5 percent (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl) propanoic acid when stored at about 40° C. and about 75% relative humidity for six months.

Another embodiment encompasses a tablet comprising telotristat or a pharmaceutically acceptable salt thereof, which forms less than 0.5 or 0.4 percent (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid when stored at about 40° C. and about 75% relative humidity for three months.

Another embodiment encompasses a granule comprising telotristat etiprate, lactose, hydroxyl propyl cellulose, croscarmellose sodium, magnesium stearate, and silicon dioxide.

Another embodiment encompasses a method of making a tablet, which comprises: combining granules comprising intragranular ingredients with at least one extragranular ingredient, and compressing the granules to provide a tablet; wherein the intragranular ingredients comprise telotristat or a pharmaceutically acceptable salt thereof, magnesium stearate, and lactose; and at least one extragranular ingredient is lactose.

4. BRIEF DESCRIPTION OF THE FIGURES

Certain aspects of the invention can be understood with reference to the appended figures.

FIG. 1 shows an X-ray powder diffraction (XRPD) pattern of a crystalline form of telotristat. The diffractogram was obtained using a Rigaku MiniFlex diffractometer (copper Kα radiation).

Figure 2:
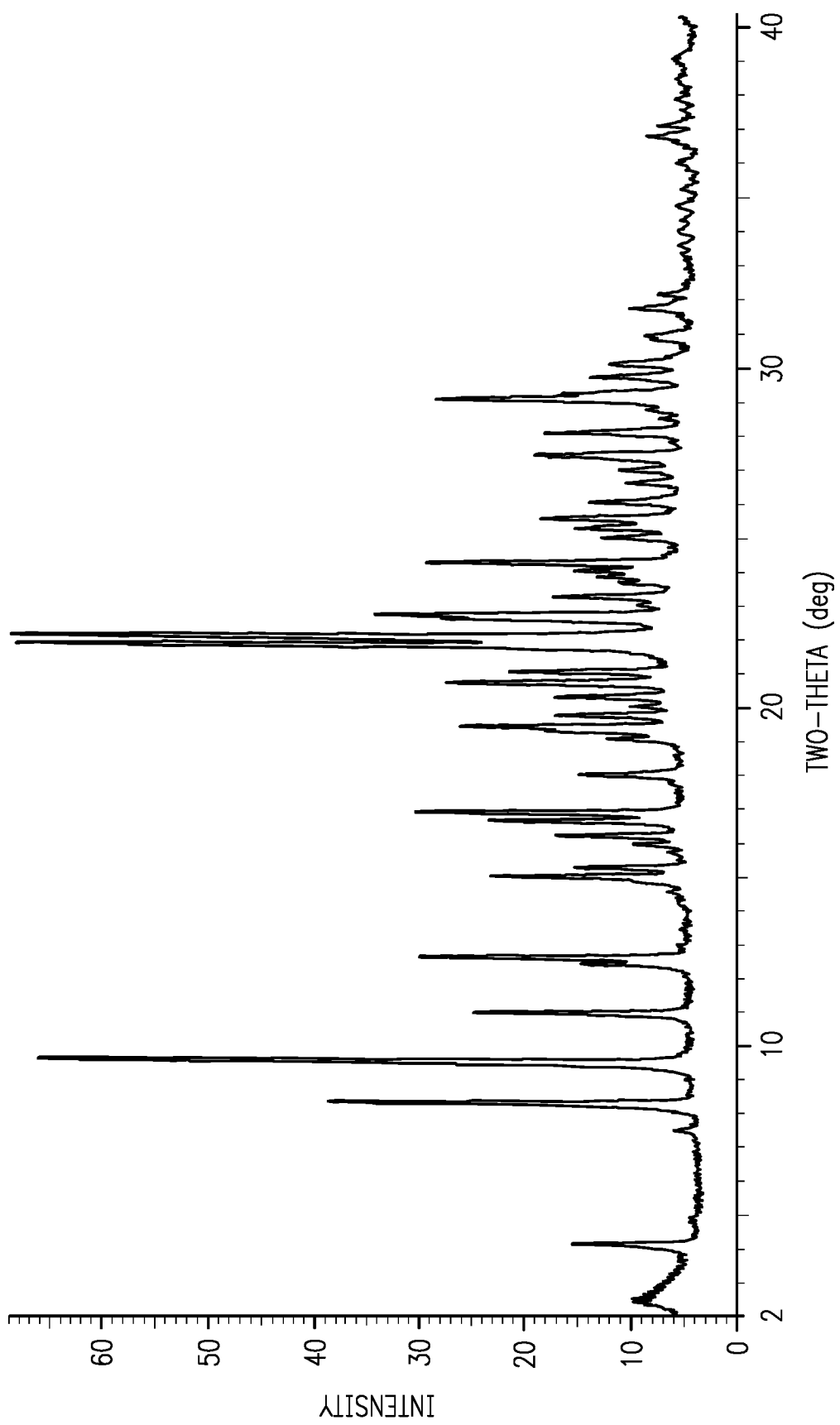

FIG. 2 provides an XRPD pattern of a crystalline form of telotristat etiprate. The diffractogram was obtained using a Bruker D8 Advance (copper Kα radiation).

Figure 3:
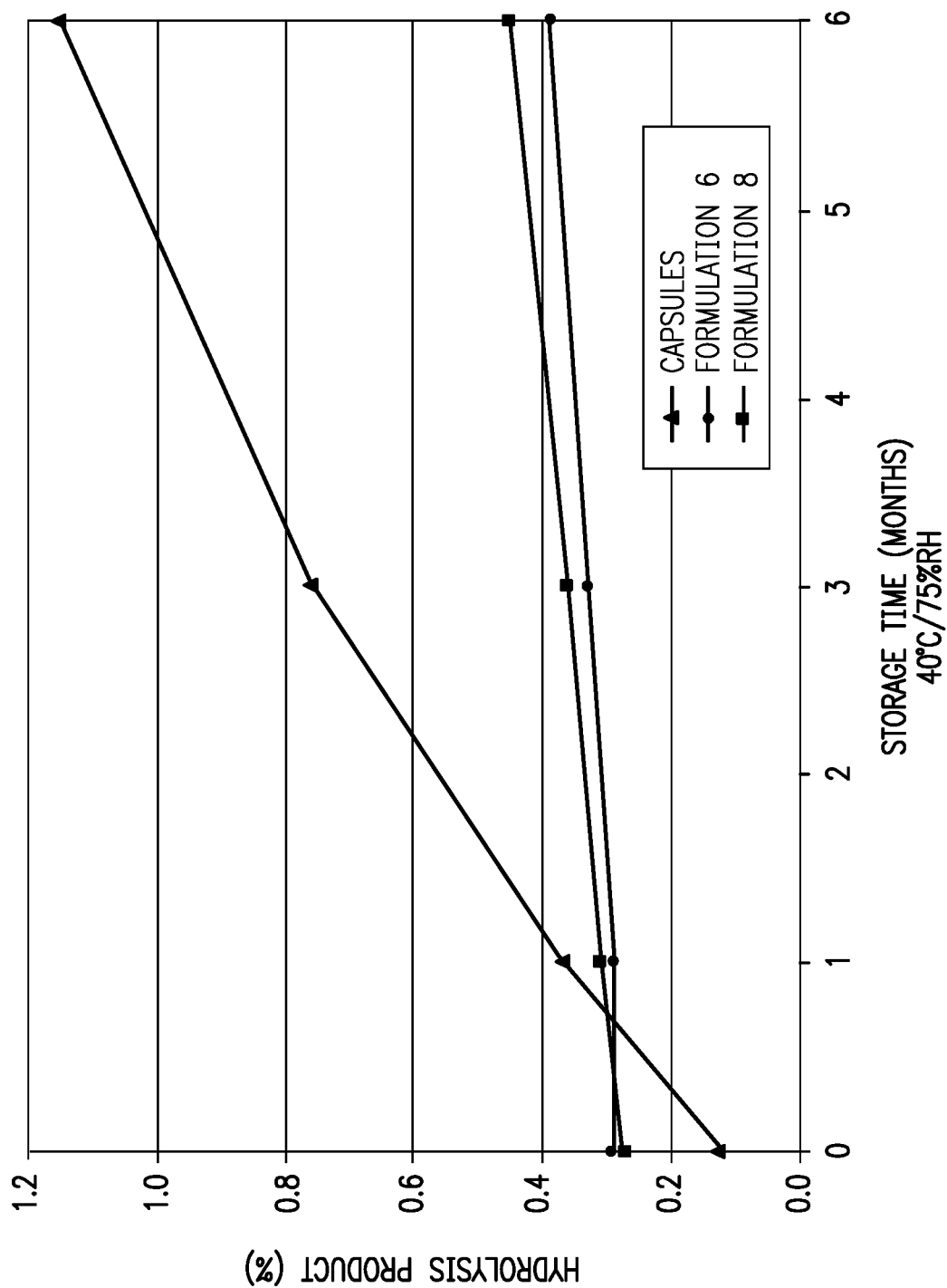

FIG. 3 shows the effects of temperature, humidity and time on the formation of the hydrolysis product (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl) phenyl)propanoic acid in different dosage forms of telotristat.

5. DETAILED DESCRIPTION OF THE INVENTION

This invention is directed to solid pharmaceutical dosage forms in which an active pharmaceutical ingredient (API) is (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate (telotristat):

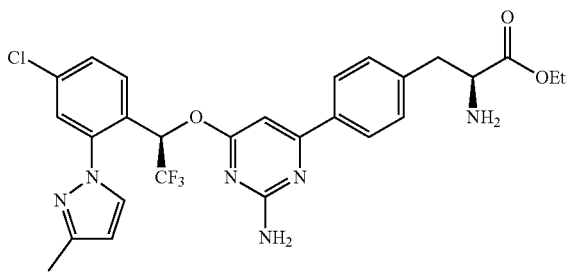 [SMILES: CCOC(=O)[C@@H](N)Cc1ccc(-c2cc(O[C@H](c3ccc(Cl)cc3-n3ccc(C)n3)C(F)(F)F)nc(N)n2)cc1]

or a pharmaceutically acceptable salt thereof. The compound, its salts and crystalline forms can be obtained by methods known in the art. See, e.g., U.S. Pat. No. 7,709,493.

Particular dosage forms comprise crystalline telotristat freebase. One form of this compound has a melting point of about 104° C. as determined by differential scanning calorimetry (DSC) (onset temperature). As used in connection with DSC temperatures, the term "about" means ±3° C. This form provides an X-ray powder diffraction (XRPD) pattern that contains peaks at about 10.7, 12.2, 12.8, 17.7 and/or 22.0 degrees 2θ. As used in connection with XPRD peaks, the term "about" means ±0.3 degrees 2θ. As those skilled in the art are well aware, the relative intensities of peaks in an XRPD pattern of a crystalline material can vary depending on how the sample is prepared and how the data is collected. With this in mind, an example of an XRPD pattern of this crystalline form is provided in FIG. 1.

Particular dosage forms comprise the hippurate salt of telotristat (telotristat hippurate; telotristat etiprate). A particular crystalline form of this salt has a melting point of about 142° C. (DSC onset temperature, with a peak at about 147° C.). A particular crystalline form provides an XRPD pattern that contains peaks at about 8.2, 9.5, 12.6, 16.9, 21.8, 22.0, 22.7, 24.3 and/or 29.1 degrees 2θ. An example of an XRPD pattern of this form is provided in FIG. 2.

When contacted with water, telotristat can hydrolyze to form (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid. Preferred dosage forms of this invention minimize this degradation. FIG. 3 shows the difference between two tablets of the invention—formulations 6 and 8, described in the examples below—and a capsule dosage form that was used in human Phase 1 and 2 clinical trials. The capsules contained a mixture of 250 mg telotristat and 2% magnesium stearate. Both tablet formulations are clearly more stable than the capsule formulation.

The bioavailability of an API can greatly depend on the formulation in which it is delivered to a patient. Here, tablets that rapidly disintegrate when administered to a patient are desired. Particular non-coated tablets of this invention have a disintegration time of less than 2.3, 2.0, or 1.8 minutes in water, or less than 4.0, 3.0, or 2.7 minutes in 0.1 N HCl. Particular-film coated tablets of the invention have a disintegration time of less than 5.5, 4.5, or 4.0 minutes in water, or less than 5.4, 5.0, or 4.8 minutes in 0.1 N HCl. As used herein, the term "disintegration time" refers to disintegration time in 100 mL of purified water or 0.1 N HCl as measured according to test USP <701>. The disintegration of a tablet can be affected by the disintegrants it contains. Examples of disintegrants include alginates, celluloses, croscarmellose sodium, crospovidone, and sodium starch glycolate. A preferred disintegrant is croscarmellose sodium.

The ability of a tablet to rapidly disintegrate or dissolve must be balanced, however, with the necessity that the tablet not fall apart in its packaging. Thus, particular tablets of the invention have a hardness greater than 8, 9, or 10 kP, and a friability of less than 0.4, 0.3, or 0.25 (percent loss).

The hardness and stability of a tablet are affected by the excipients it contains. The excipients can also affect the ease with which a tablet is made (e.g., by affecting how well the ingredients from which it is made flow and compress). Particular tablets of the invention comprise telotristat etiprate, cellulose, lactose, croscarmellose sodium, magnesium stearate, and silicon dioxide This invention encompasses methods of making solid dosage forms of telotristat and salts thereof that limit the compound's exposure to water and address the poor flow properties exhibited by many of its forms. In a particular embodiment, roller compaction is used to prepare a granular material ("granulate") made of up granules comprising the compound, which is then combined with additional excipients and compressed to provide a tablet core. The core is then optionally coated to increase the stability of the resulting tablet.

Particulate granules comprise telotristat etiprate, hydroxypropyl cellulose, lactose, croscarmellose sodium, magnesium stearate, and silicon dioxide. Preferred granulates flow and compress well, allowing the ready manufacture of tablets possessing the desired hardness, stability, and disintegration properties described herein.

The solid dosage forms (e.g., tablets) of the invention can be packaged by methods and using containers known in the art. The packaging material may form a plurality of divided containers such as a divided bottle or a divided foil packet. The container can be in any conventional shape or form as known in the art which is made of a pharmaceutically acceptable material, for example a paper or cardboard box, a glass or plastic bottle or jar with or without desiccant, a re-sealable bag (for example, to hold a "refill" of tablets for placement into a different container), or a blister pack (e.g., Aclar blisters or foil/foil blisters) with individual doses for pressing out of the pack according to a therapeutic schedule. In a preferred embodiment, tablets are stored in an induction-sealed HDPE bottle with a desiccant pack.

6. EXAMPLES

6.1. Tablet and Ingredient Characterization

Disintegration testing was performed as per USP <701> using the test for uncoated tables and plain coated tablets. The disintegration was performed in 1000 mL purified water or 0.1 N HCl. Disintegration endpoint was determined visually.

Dissolution was determined in 900 mL of 0.1 N HCl at 37° C. using USP Apparatus 2 (paddles) set at 50 rpm. Filtrates of the dissolution test solution were collected at specific time intervals. The samples were analyzed by high performance liquid chromatography (HPLC) using a PhenomenexSynergi 4µ Max-RP column and a mobile phase of 70/30/0.2 (v/v/v) methanol/water/phosphoric acid at a flow rate of 1.0 mL/min. The HPLC system utilized ultraviolet (UV) detection at a wavelength of 237 nm.

Granulation particle size was determined using a sieve method, wherein the tare weight of each of several sieves (mesh 25, 40, 60, 100, 140, 230, and Fines) was recorded, the sieves were stacked in order of the coarsest sieve on top and the finest on bottom, and approximately 5 grams of the granulate material was transferred to the top sieve. The assembly was secured and placed in an ATM Sonic sifter, the pulse amplitude and sift amplitudes both set to 5. After 5 minutes, the assembly was removed and the individual sieves weighed. Flow properties were determined using a J.R. Johanson Flow Indicizer.

6.2. General Tablet Preparation

Tablets comprising 300 mg (measured as free base) of the API telotristat in the hippurate salt form were made in two general steps. First, granules comprising crystalline telotristat etiprate and selected excipients (intragranular components) were prepared. The material was compressed using a roller compactor and milled. The intragranular material was then combined with additional excipients ("extragranular components"), and the resulting mixture was compressed to provide the tablets. In some cases, the tablets were coated.

Batches were prepared by screening all intragranular materials except magnesium stearate through a 20-mesh screen. Components were blended in an appropriately sized V-blender for 10 minutes. Intragranular magnesium stearate was combined with a portion of the blend and co-screened through a 20-mesh screen. The screened magnesium stearate blend was then charged into the V-blender and blended for an additional three minutes. The blend was then roller compacted using a Vector TF-Mini roller compactor with a target ribbon thickness of 1.5 mm. The ribbons were milled by sequentially oscillating them through a 14-mesh and 20-mesh screen. All extragranular components except magnesium stearate were combined and screened through a 20-mesh screen. Approximately half of the granulation was charged into the V-blender followed by the screened extragranular components. The remaining half of the granulation was charged into the V-blender and blended for five minutes. A small portion of the blend was removed and combined with the magnesium stearate and passed through a 20-mesh screen. The magnesium stearate blend was charged into the V-blender and blended for an additional three minutes. The final blend was compressed into LX-1606 300-mg tablets. Some batches were film coated in a Strea 1 Fluid Bed Coater with Opadry 2 Clear to a 4% weight gain.

6.3. Formulation 1

In this example, tablets were made from the ingredients listed below in Table 1:

TABLE 1

| Intragranular Components (mg/tablet) | |
|---|---|
| API | 402.12* |
| Citric Acid, Anhydrous | 83.79 |
| Lactose, Anhydrous | 90.77 |
| Hydroxy Propyl Cellulose | 34.91 |
| Croscarmellose Sodium | 20.95 |
| Magnesium Stearate | 3.49 |
| Extragranular Components (mg/tablet) | |
| Lactose, Anhydrous | 34.28 |
| Croscarmellose Sodium | 20.95 |
| Colloidal Silicon Dioxide | 3.49 |
| Magnesium Stearate | 5.24 |
| Core Tablet Total | 700.0 |

*Equivalent to 300 mg telotristat free base

First, the intragranular components were mixed and roller compacted with a roller pressure of 70 kg/cm². The ribbons were 0.99-1.42 mm in thickness. A bench-top ribbon disintegration test was performed by placing a one inch section of ribbon in a beaker containing approximately 500 mL of DI water and allowed to disintegrate. The ribbon disintegrated in 12.5 minutes. Inspection of the roller compactor rollers indicated that some sticking had occurred. Ribbons were milled by oscillating sequentially through a 14-mesh and 20-mesh screen. The granulation was blended with extragranular components and physical tests were performed. The granules flowed poorly, and the initial tablets exhibited weight variations and low average tablet weight. Striations and chipping were also observed on the first tablets produced. Initial tablets also failed a friability test loss limit of ≤0.8%, yet sticking prevented the compression forces from being increased to improve the friability. These problems were addressed by increasing the extragranular magnesium stearate by 0.25%, and blended with the remaining blend (the amount of magnesium stearate shown in Table 1 reflects this additional amount). The resulting final blend was compressed into tablets (0.300"×0.680" capsule shaped tooling). No further sticking was observed.

Characteristics of the granulation and tablets are shown below in Table 2:

TABLE 2

| | |
|---|---|
| Approximate Ribbon Disintegration Time (min) | 12.5 |
| Bulk Density (g/mL) | 0.6644 |
| Tapped Density (g/mL) | 0.886 |
| Average Flow Rate Index (kg/sec) | 0.511 |
| Core Hardness Range (kP) | 8.1-12.0 |
| Average Core Weight (g) | 0.679 |
| Average Tablet Thickness (mm) | 5.65 |
| Tablet Friability (% loss) | 0.3 |

The tablets' dissolution properties are shown below in Table 3:

TABLE 3

| Time (min) | % Drug Released |
|---|---|
| 10 | 50.7 |
| 20 | 81.6 |
| 30 | 94.6 |
| 45 | 98.2 |
| 60 | 98.2 |

6.4. Formulation 2

In this example, tablets were made from the ingredients listed below in Table 4:

TABLE 4

| Intragranular Components (mg/tablet) | |
|---|---|
| API | 403.13 |
| Citric Acid, Anhydrous | 84.00 |
| Microcrystalline Cellulose | 89.25 |
| Hydroxy Propyl Cellulose | 35.00 |
| Croscarmellose Sodium | 28.00 |
| Magnesium Stearate | 5.25 |
| Extragranular Components (mg/tablet) | |
| Microcrystalline Cellulose | 18.62 |
| Croscarmellose Sodium | 28.00 |
| Colloidal Silicon Dioxide | 3.50 |
| Magnesium Stearate | 5.25 |
| Core Tablet Total | 700.0 |

First, the intragranular components were mixed and roller compacted with a roller pressure of 45 kg/cm². The ribbon thicknesses ranged from 1.16-1.46 mm. Bench-top ribbon disintegration test resulted in a disintegration time of 3 minutes. Some sticking was noted during the roller compaction of the blend. The ribbons were milled by oscillating sequentially through a 14-mesh and 20-mesh screen. The ribbons were hard and more difficult to mill. Approximately 0.75% of the batch did not pass through the oscillator. The granulation was blended with extragranular components and physical tests were performed. Granulation exhibited poor flow characteristics, although the compression was manageable. Some sticking to tablet punches was observed initially during compression, which subsided after the punches were cleaned. The tablets exhibited a dull appearance, which did not improve when the compression force was increased.

6.5. Formulation 3

In this example, tablets were prepared using the ingredients listed below in Table 5:

TABLE 5

| Intragranular Components (mg/tablet) | |
|---|---|
| API | 403.13 |
| Citric Acid, Anhydrous | 84.00 |
| Microcrystalline Cellulose | 89.25 |
| Hydroxy Propyl Cellulose | 35.00 |
| Crospovidone | 28.00 |
| Magnesium Stearate | 5.25 |

| Extragranular Components (mg/tablet) | |
|---|---|
| Microcrystalline Cellulose | 18.62 |
| Crospovidone | 28.00 |
| Colloidal Silicon Dioxide | 3.50 |
| Magnesium Stearate | 5.25 |
| Core Tablet Total | 700.0 |

The mixture of intragranular components was roller compacted with a roller pressure of 50 kg/cm$^2$. The ribbon thicknesses ranged from 1.40-1.90 mm. Bench-top ribbon disintegration test resulted in an undesirable disintegration time of 11 minutes. Some sticking was observed during the roller compaction process. The ribbons were similar to Formulation 2 and were difficult to mill. Granulation was blended with extragranular components and physical tests were performed. The granulation exhibited poor flow, and some rat-holing was observed in the hopper during compression, which was overcome by agitating the hopper. Tablet compression was completed with no observable problems. However, tablet disintegration testing in water and 0.1N HCl resulted in disintegration times significantly longer than those observed the other formulations, suggesting that in these formulations, crospovidone is a less effective disintegrant than croscarmellose sodium.

6.6. Formulation 4

In this example, granules were prepared using the ingredients listed below in Table 6:

TABLE 6

| Intragranular Components (mg/tablet) | |
|---|---|
| API | 403.13 |
| Citric Acid, Anhydrous | 84.00 |
| Mannitol | 44.45 |
| Microcrystalline Cellulose | 44.80 |
| Hydroxy Propyl Cellulose | 35.00 |
| Crospovidone | 28.00 |
| Magnesium Stearate | 5.25 |

Because the disintegration tests run on the ribbons made from this mixture showed a disintegration time of 11 minutes, further work on this formulation was not done.

6.7. Formulation 5

In this example, tablets were prepared using the ingredients listed below in Table 7:

TABLE 7

| Intragranular Components (mg/tablet) | |
|---|---|
| API | 403.13 |
| Citric Acid, Anhydrous | 84.00 |
| Mannitol | 44.45 |
| Hydroxy Propyl Cellulose | 35.00 |
| Croscarmellose Sodium | 28.00 |
| Magnesium Stearate | 5.25 |

TABLE 7-continued

| Extragranular Components (mg/tablet) | |
|---|---|
| Microcrystalline Cellulose | 18.62 |
| Croscarmellose Sodium | 28.00 |
| Colloidal Silicon Dioxide | 3.50 |
| Magnesium Stearate | 5.25 |
| Core Tablet Total | 700.0 |

The mixture of intragranular components was roller compacted with a roller pressure of 50 kg/cm$^2$. The ribbon thickness ranged from 1.37-1.83 mm. Bench-top ribbon disintegration time was 1 minute. Minor sticking was observed throughout the roller compaction process. The granulation was blended with the extragranular components and physical tests were performed. The granulation exhibited poor flow, but tablet compression was completed with no observable problems. The formulation was capable of achieving hardnesses exceeding 18 kP. Tablet disintegration testing in water and 0.1N HCl resulted in acceptable disintegration times for an immediate release tablet: 2.0 minutes in water, 4.0-5.25 minutes in 0.1N HCl. However, assay and related substance testing indicated that an unacceptable amount of what is believed to be a hydrolysis product of the API increased significantly at the one-month time point when stored at 40° C./75% RH without desiccant. An additional batch of Formulation 5 was manufactured, and in this case, the resulting tablets were coated with Opadry Clear. The granulation lot was roller compacted with a roller pressure of 50 kg/cm$^2$, affording a ribbon thickness ranging from 1.24-1.57 mm. Bench-top ribbon disintegration time was 3.25 minutes. Minor sticking to the rollers was observed throughout the roller compaction process. Blend was also observed to be sticking to the walls of the hopper and exhibited poor flow. The granulation was blended with the extragranular components and physical tests were performed. Sticking was observed after 5 minutes of tablet compression. The punches were cleaned and compression was restarted, but tablet sticking resumed immediately, suggesting that the granulation may require additional lubrication or increased lubrication time to overcome sticking issues. The resulting tablets were coated to a 4% weight gain. The dissolution profile of these tablets was acceptable, although the disintegration times in water and 0.1 N HCl were significantly longer than the uncoated tablets. Assay and related substance testing indicated that coating the tablet to a theoretical weight gain of 4% decreases the level of degradation, a level which is further decreased with the use of desiccant.

6.8. Formulation 6

In this example, tablets were prepared using the ingredients listed below in Table 8:

TABLE 8

| Intragranular Components (mg/tablet) | |
|---|---|
| API | 403.13 |
| Mannitol | 86.45 |
| Microcrystalline Cellulose | 86.45 |
| Hydroxy Propyl Cellulose | 35.00 |
| Croscarmellose Sodium | 28.00 |
| Magnesium Stearate | 5.25 |

| Extragranular Components (mg/tablet) | |
|---|---|
| Microcrystalline Cellulose | 18.97 |
| Croscarmellose Sodium | 28.00 |

TABLE 8-continued

| | |
|---|---|
| Colloidal Silicon Dioxide | 3.50 |
| Magnesium Stearate | 5.25 |
| Core Tablet Total | 700.0 |

The mixture of intragranular components was roller compacted with a roller pressure of 50 kg/cm$^2$. The ribbon thickness ranged from 1.11-1.52 mm. Bench-top ribbon disintegration time was 1 minute. Very little sticking was observed throughout the roller compaction process. Although the granulation exhibited poor flow, it was blended and compressed into tablets, during which some sticking was observed. Tablets exhibited some chipping during friability testing. Dissolution and disintegration times were: 1.3-1.5 minutes in water; 1.5-2.8 minutes in 0.1 N HCl. These tablets particularly stable (0.23 area percent after 1 month at 40° C./75% relative humidity), and more so when stored with desiccant (0.16 area percent after 1 month at 40° C./75% relative humidity).

6.9. Formulation 7

In this example, tablets were prepared using the ingredients listed below in Table 9:

TABLE 9

| Intragranular Components (mg/tablet) | |
|---|---|
| API | 403.13 |
| Citric Acid, Anhydrous | 84.00 |
| Lactose, Anhydrous | 80.50 |
| Hydroxy Propyl Cellulose | 35.00 |
| Croscarmellose Sodium | 28.00 |
| Magnesium Stearate | 5.25 |

| Extragranular Components (mg/tablet) | |
|---|---|
| Lactose, Anhydrous | 27.37 |
| Croscarmellose Sodium | 28.00 |
| Colloidal Silicon Dioxide | 3.50 |
| Magnesium Stearate | 5.25 |
| Core Tablet Total | 700.0 |

The mixture of intragranular components was roller compacted with a roller pressure of 50 kg/cm$^2$. The ribbon thickness ranged from 1.45-1.63 mm. Bench-top ribbon disintegration time was 3 minutes. Very little sticking was observed during roller compaction. Granulation, which exhibited poor flow, was blended and compressed into tablets. Sticking was observed on the punch faces and die walls during tablet compression. Chipping was also noted during friability testing. Dissolution and disintegration times were acceptable, although assay and related substance testing indicated a significant increase in apparent API hydrolysis product when stored for one month under accelerated conditions without desiccant (1.01 area percent after 1 month at 40° C./75% relative humidity). Desiccant decreased the observed level of hydrolysis product to 0.16.

6.10. Formulation 8

In this example, tablets were prepared using the ingredients listed below in Table 10:

TABLE 10

| Intragranular Components (mg/tablet) | |
|---|---|
| API | 403.13 |
| Lactose, Anhydrous | 164.50 |

TABLE 10-continued

| | |
|---|---|
| Hydroxy Propyl Cellulose | 35.00 |
| Croscarmellose Sodium | 35.00 |
| Magnesium Stearate | 5.25 |

| Extragranular Components (mg/tablet) | |
|---|---|
| Lactose, Anhydrous | 27.37 |
| Croscarmellose Sodium | 21.00 |
| Colloidal Silicon Dioxide | 3.50 |
| Magnesium Stearate | 5.25 |
| Core Tablet Total | 700.0 |

The mixture of intragranular components was roller compacted with a roller pressure of 55 kg/cm$^2$. The ribbon thickness ranged from 1.07-1.52 mm. The material processed very well, yielding long ribbons. Bench-top ribbon disintegration time was 2.5 minutes. Approximately 2% of the ribbons did not pass through the 20-mesh oscillating screen. Granulation was blended and compressed into tablets. The blend compressed well and no sticking was observed. Some minor picking was observed.

Physical characteristics of the granulation and tablets are shown below in Table 11:

TABLE 11

| | |
|---|---|
| Approximate Ribbon Disintegration Time (min) | 2.5 |
| Core Hardness Range (kP) | 8.5-11.9 |
| Average Core Weight (g) | 0.711 |
| Average Tablet Thickness (mm) | 6.03 |
| Tablet Friability (% loss) | 0.3 |

The tablets' disintegration profile was acceptable: uncoated tablets disintegrated in 1.8-2.3 minutes in water and 2.7-4.0 minutes in 0.1N HCl; coated tablets disintegrated in 3.1-5.5 minutes in water and 4.4-5.4 minutes in 0.1N HCl. The dissolution profile of the tablets is shown below in Table 12:

TABLE 12

| | Mean % Label Claim | |
|---|---|---|
| Time (min) | Uncoated Tablets | Coated Tablets |
| 10 | 93.6 | 84.6 |
| 20 | 98.3 | 94.7 |
| 30 | 99.5 | 96.0 |
| 45 | 99.8 | 96.0 |

This formulation performed well during the stability study, with little of the hydrolysis product observed in the uncoated tablets without desiccant (0.39 area percent after 1 month at 40° C./75% relative humidity), in uncoated tablets with desiccant (0.32 area percent after 1 month at 40° C./75% relative humidity), in coated tablets with desiccant (0.31 area percent after 1 month at 40° C./75% relative humidity), in Aclar blisters (0.42 area percent after 1 month at 40° C./75% relative humidity), and in foil/foil blisters (0.39 area percent after 1 month at 40° C./75% relative humidity).

6.11. Stability Determination

The stability of tablets was determined by a reverse-phase HPLC-based method employing the following conditions:

| Column: | Waters XTerra MS C18 (4.6 × 150 mm, 3.5 μm Particle Size) |
| --- | --- |
| Column Temperature: | 40° C. |
| Autosampler Temperature: | 5° C. |
| Mobile Phase A: | 0.05% TFA in Water |
| Mobile Phase B: | 0.05% TFA in ACN |
| Flow Rate: | 1.0 mL/minute |
| Detection Wavelength: | 254 nm |
| Injection Volume: | 5 μL |
| Data Acquisition Time: | 41 minutes |
| Data Output: | Ensure Peak is on Scale |

The pump program used was:

| Time (min) | % Mobile Phase A | % Mobile Phase B |
| --- | --- | --- |
| 0 | 100 | 0 |
| 30 | 5 | 95 |
| 35 | 5 | 95 |
| 36 | 100 | 0 |
| 41 | 100 | 0 |

A standard solution was prepared by dissolving telotristat etiprate in THF with a concentration of approximately 0.25 μg/mL.

Samples were prepared from 300 mg tablets as follows: 1) at least 4 tablets were weighed; 2) then crushed using a mortar and pestle; 3) an amount of equivalent to about 50 mg drug substance (i.e., about 117 mg) was weighed and transferred to a 100-mL volumetric flask; 4) then diluted to about 1/2 to 2/3 volume with diluent (THE); 5) the flask was then placed on a shaker for at least 20 minutes at low speed; 6) the volume was then further diluted with diluent and mixed well; 7) an aliquot was centrifuged for about 5 minutes at approximately 3000 RPM; 8) an aliquot of the supernate was then withdrawn for injection; 9) steps 3 through 8 were repeated for a total of two replicates for injection; 10) the average retention time of the API peak was then determined for the first six injections of the standard solution; and 2) the ratio of the retention time of any peaks in the sample preparation to the average retention time of the API peak in the first six injections of the standard was then calculated.

Potency was determined using the following equation:

$$\text{API (mg) per tablet} = (A_{sample} * W_{total}) / (RF_{std} * W_{sample} * N_{total}) * DF_{sample}$$

where: $A_{sample}$=API sample peak area; $W_{total}$=total weight of the tablets (mg); $DF_{sample}$=sample dilution volume in mL (100 mL for the 300-mg tablets); $RF_{std}$=standard average response factor (1$^{st}$ 6 injections); $W_{sample}$=Individual sample weight (mg); and $N_{total}$=Number of tablets used (at least 4). Individual impurities were determined as a percent of the total integrated peak area.

All references cited herein (e.g., patents and patent applications) are incorporated herein in their entireties.

What is claimed is:

1. A tablet made from intragranular and extragranular components, comprising: intragranular components being 403.13 mg of (S)-2-amino-3-(4-(2-amino-6-((R)-1-(4-chloro-2-(3-methyl-1H-pyrazol-1-yl)-phenyl)-2,2,2-trifluoroethoxy)pyrimidin-4-yl)phenyl)propanoic hippurate, 164.50 mg of lactose anhydrous, 35.00 mg of hydroxy propyl cellulose, 35.00 mg of croscarmellose sodium and 5.25 mg of magnesium stearate, and the extragranular components being 27.37 mg of lactose anhydrous, 21.00 mg of croscarmellose sodium, 3.5 mg of colloidal silicon dioxide and 5.25 mg of magnesium stearate.

\* \* \* \* \*